(12) United States Patent
Rehder et al.

(10) Patent No.: US 6,588,432 B1
(45) Date of Patent: Jul. 8, 2003

(54) TISSUE EXPANDER MAGNETIC INJECTION PORT

(75) Inventors: Carey D. Rehder, Woodbury, MN (US); Jason P. Porter, Mound, MN (US); Deron J. Singer, Burnsville, MN (US)

(73) Assignee: PMT Corporation, Chanhassen, MN (US)

( * ) Notice: Subject to any disclaimer, the term of this patent is extended or adjusted under 35 U.S.C. 154(b) by 71 days.

(21) Appl. No.: 09/784,289

(22) Filed: Feb. 15, 2001

(51) Int. Cl.[7] ............................................. A61B 19/00
(52) U.S. Cl. ........................... 128/899; 128/898; 623/8
(58) Field of Search ................................. 128/899, 898; 623/7–8, 901; 604/103, 96.01

(56) References Cited

U.S. PATENT DOCUMENTS

| | | | |
|---|---|---|---|
| 3,583,387 A | * 6/1971 | Garner et al. | 600/561 |
| 4,671,255 A | * 6/1987 | Dubrul et al. | 128/899 |
| 4,685,447 A | 8/1987 | Iversen | |
| 4,840,615 A | * 6/1989 | Hancock et al. | 128/899 |
| 5,146,933 A | * 9/1992 | Boyd | 128/899 |
| 5,632,777 A | * 5/1997 | Petrick | 128/898 |
| 6,171,299 B1 | * 1/2001 | Bonutti | 606/1 |
| 6,355,212 B1 | * 3/2002 | Antolotti | 420/117 |

* cited by examiner

*Primary Examiner*—Gregory Huson
*Assistant Examiner*—Amanda R. Flynn
(74) *Attorney, Agent, or Firm*—Anthony G. Eggink

(57) ABSTRACT

A magnetic injection port assembly for a tissue expander system or similar inflatable medical device. The injection port assembly includes an injection port body having a cavity, a needle guard assembly, and a magnetic material therein. The needle guard assembly is positioned to prevent a hypodermic needle from passing through the medical device or interfering with the magnetic material. The magnetic material is affixed to the injection port body outside the cavity and the needle guard assembly. The magnetic material is spatially aligned with the region of the body into which the needle should be inserted so that this region may be located by locating the magnet with an external, non-invasive magnetic detection device.

20 Claims, 3 Drawing Sheets

TISSUE EXPANDER MAGNETIC INJECTION PORT

BACKGROUND OF THE INVENTION

This invention relates generally to injection fill ports used with tissue expander systems and similar inflatable medical devices. Particularly, this invention relates to an improved injection port structure wherein a magnetic material is incorporated in an injection port assembly. The magnetic material is positioned so that the injection port can be easily and accurately located by noninvasive means. The magnetic material is positioned in the port structure so that it does not interfere with the use of a hypodermic needle for filling purposes.

A tissue expander or similar inflatable medical device is typically implanted under a patient's skin. In order to expand the tissue structure, fluid is injected using a hypodermic needle or similar device by filling an injection port which is in communication with the tissue expander. As far as is known, the prior art has not proposed or developed a structure which incorporates a magnet with an injection port so that the magnet does not interfere with the injection of a hypodermic needle as does the present invention. For example, in the prior art, U.S. Pat. No. 4,685,447 teaches using a metal plate and X-ray procedure to find an injection port of an implanted tissue expander system, thus exposing a patient to radiation. U.S. Pat. No. 4,671,255 describes a tissue expander system that incorporates a magnet or magnetically detectable material into the injection port by mounting the magnetic material in a recess of the needle guard assembly. The needle guard and/or magnetic material has the propensity to obstruct the end of a hypodermic needle which is injected into the injection port. The latter patent also teaches the use of an inverted hemispheric member to achieve a self-sealing injection port, which complicates the injection port assembly. The present invention overcomes these shortcomings of the prior art by incorporating several structural improvements.

The present invention incorporates a magnet or magnetically detectable material into an injection port of a tissue expander system or into an inflatable medical device for port detection by an external detection means that is constructed and arranged to sense magnetic fields. The magnetic material or element which generates a magnetic field is permanently affixed in the injection port so that its location can be accurately determined by non-invasive external means, thus providing the user with a rapid, convenient, and precise means for locating the injection port. Further, the magnet material is incorporated in the structure which does not interfere with the needle used for filling the tissue expander system.

An object of the present invention is to provide the magnetic material in the injection port but outside of the injection port cavity so that the magnetic material does not obstruct the end of a needle while injecting fluid into the port. Another object of this invention is to completely enclose the magnetic material in a polymer to protect it from environmental exposure. Another object of this invention is to use magnetic material that has been surface treated to prevent the magnetic material from corroding. Yet another objective of this invention is to develop an injection port that is simple in design and easy to manufacture.

SUMMARY OF THE INVENTION

This invention provides a magnetic injection port for use with a tissue expander or an inflatable device for implantation. An injection port is used in communication with a tissue expander to permit the tissue expander to be filled with fluid. The tissue expander and injection port are located under the skin and must be properly located in order to permit the filling or inflation of the tissue expander.

The invention incorporates a magnet or magnetically detectable material into the injection port of a tissue expander system or similar inflatable medical device for port detection by an external detection means that is constructed and arranged to sense magnetic fields. The injection port has a body defining a cavity into which the end of a hypodermic needle or similar device is inserted to inject fluid into the cavity. When a desired volume of fluid has been injected into the cavity, fluid flows under pressure via a means of fluid communication, the only means of egress from the cavity, from the injection port into the tissue expander or other medical device. The region of the injection port body into which the needle is inserted is self-sealing to such punctures.

A needle guard member is positioned spacially from and on the opposite side of the injection port body from where the needle enters, to prevent the needle from puncturing the injection port and entering into the tissue expander of the patient. A magnetic material is affixed in the injection port body outside the injection port cavity and the needle guard member. The magnetic material is positioned outside the injection port cavity so that its placement does not interfere with the normal and proper insertion of a needle into the injection port cavity. The magnetic material may be any shape or dimension, and made of any magnetically detectable material. For example, the magnetic material may include samarium cobalt or neodymium iron boron, a combination thereof or like material. The outermost perimeter of the magnetic material is spatially aligned with or within the perimeter of the region of the injection port into which the needle is injected, thus demarcating this region as a target for the needle. The magnetic material also has a surface treatment to prevent it from corroding, such as a nickel coating or the like, and is completely enclosed in a polymer, such as a silicone elastomer or the like, to protect it from environmental exposure.

To locate the injection port, a magnetic detection means is scanned across the region of skin containing the system to establish at least four points of reference creating a coordinate system. The location for inserting the needle is at the intersection of two line segments, each defined by a pair of the reference points established by two passes of the detection means. This intersection is where the magnetic injection port is located and where the medical procedure should be performed.

These and other benefits of this invention will become apparent from the following description by reference to the drawings.

DESCRIPTION OF THE PREFERRED EMBODIMENTS

This invention relates to a magnetic injection port assembly for use with a tissue expander or an inflatable medical device implanted beneath the skin of a patient. The magnetic injection port is useful for medical technicians, practitioners and physicians when performing various medical procedures related to the tissue expander. The incorporation of a magnet or an element which generates a magnetic field permits the medical technician, practitioner or physician to quickly, conveniently and precisely locate the injection port using a magnetic sensing probe or similar device.

Figure 1:
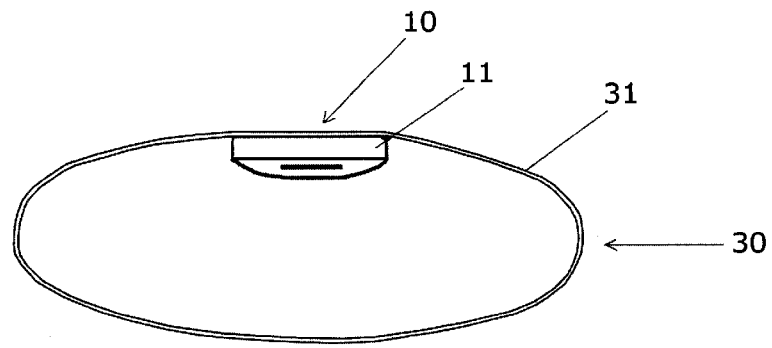
FIG. 1 is a lateral view, partially in section of the magnetic injection port of the invention and showing the injection port incorporated into a tissue expander.

FIG. 1 is a lateral view of a tissue expander system 30 which incorporates the injection port assembly 10 of the invention. The tissue expander system 30 is shown comprised of a tissue expander shell 31 and an injection port assembly 10 having an injection port body 11. The injection port assembly 10 may also be incorporated in other medical devices which may require a filling or similar procedure.

Figure 2:
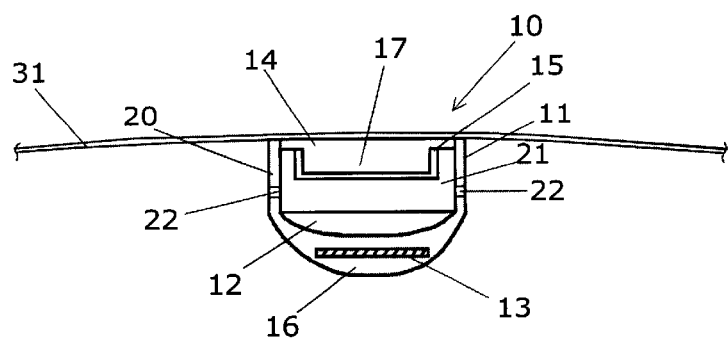
FIG. 2 is a cross-sectional view of the injection port of FIG. 1.
Figure 3:
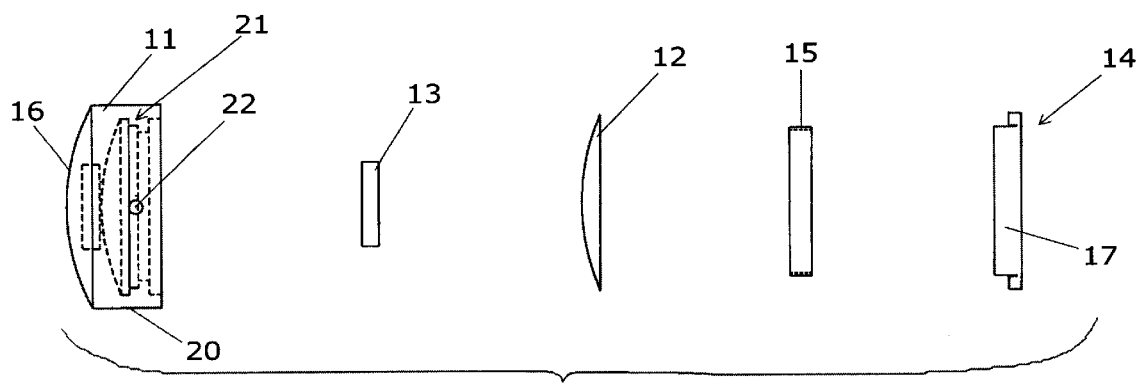
FIG. 3 is a cross sectional view showing various parts of an injection port.

Referring to FIGS. 2 and 3, the injection port assembly 10 is shown having a body 11 that is generally cylindrical in shape and which is comprised of an injection port top portion 14, an outside lateral wall 20, and a port bottom portion 16. The top portion 14 of the injection port body 11 together with the ring member 15 and needle guard member 12 define and form an injection port cavity 21. A hypodermic needle or similar device may be inserted through the top portion 14 and into the cavity 21 to inject a saline solution or other biocompatible fluid for expansion purposes. Fluid flows from the cavity 21 to the tissue expander system 30 via a means of fluid communication 22 when a desired volume of fluid has been injected into the cavity 21. The fluid communication means 22 may be one or more apertures, i.e., two, in the port assembly body. Magnetic material 13 is shown located and positioned outside the injection port cavity 21, between needle guard 12 and injection port body bottom 16.

The injection port top 14 is self-sealing to punctures and has a centrally disposed thickened portion 17 through which a hypodermic needle or similar device can be inserted into the injection port cavity 21. A needle guard assembly 12 prevents the needle from penetrating through the injection port bottom 16 of the injection port body 11 and into the tissue expander shell 31 or into the patient. Providing the magnetic material 13 outside or below cavity 21 and below needle guard 12 prevents it from interfering with the injected needle and protects it from environmental exposure.

The injection port body 11 is preferably constructed of an elastomeric material, such as silicone or the like and is preferably formed by an injection molding process. The needle guard member 12 is preferably constructed of a stainless steel, Kevlar®, HDPE or like puncture resistant material. The needle guard member 12 is shown to have a curved dish-shaped configuration which extends over and covers the bottom of the injection port cavity 21 to thereby protect the integrity of the injection port body 11 and the magnetic material 13.

Figure 4:
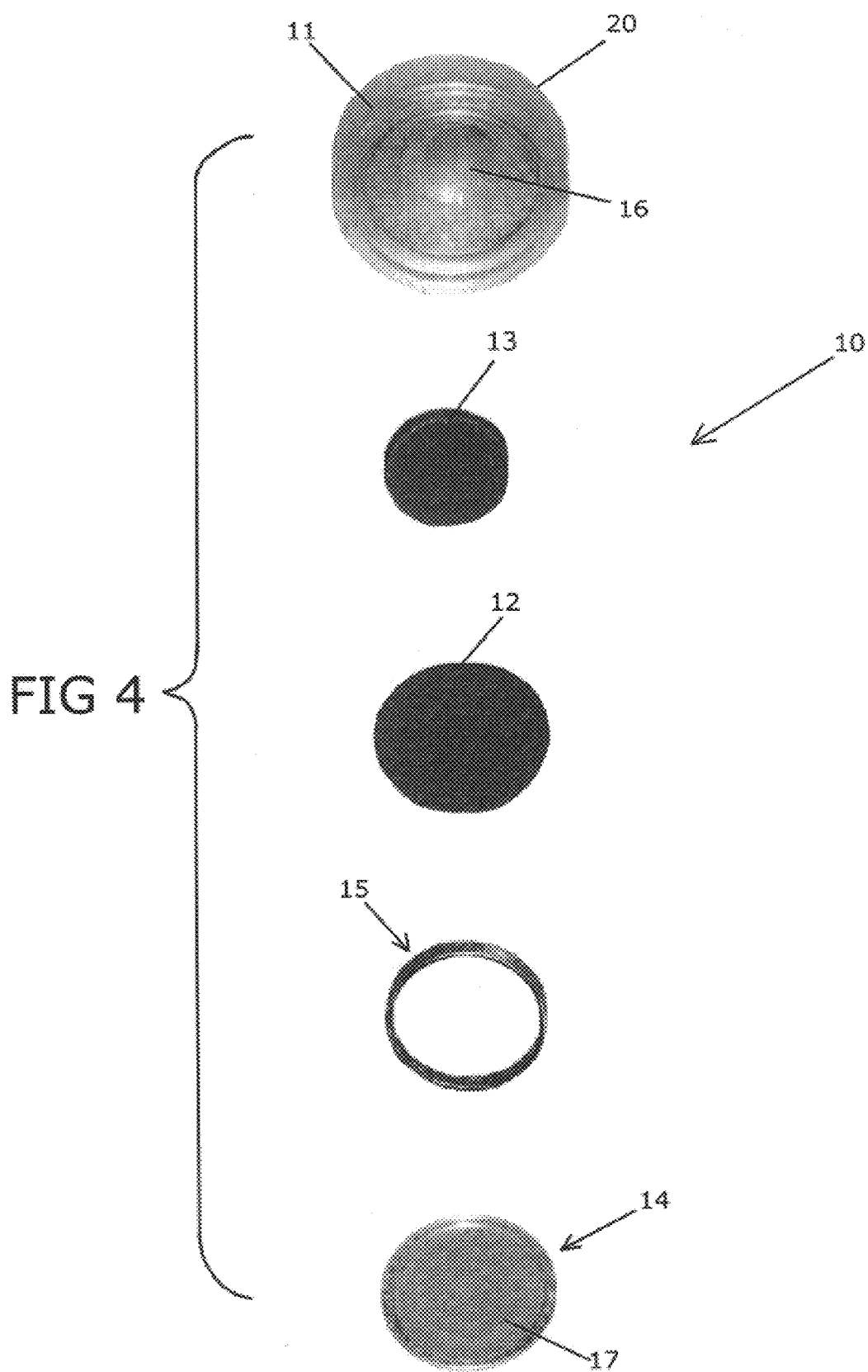
FIG. 4 is a perspective view of the parts of an injection port.

FIG. 4 shows the elements which comprise the injection port assembly 10. The assembly 10 comprises an injection port body 11, a top portion 14, a lateral wall or ring member 15, needle guard structure 12 and magnetic material 13 are shown in perspective. As also shown in FIG. 3, ring member 15 is constructed and arranged to fit around top 14. This arrangement holds the top portion 14 together and in place after several punctures and aides in the self-sealing of top portion 14. The ring member 15 is preferably constructed of stainless steel or other non-magnetic material.

The magnetic material 13 can be any desired shape or dimension constructed of any magnetically detectable material. Preferably, the magnetic material is a flat, disc shape shown as magnetic material 13. For example, the magnetic structures may be constructed of magnetic materials having cylindrical, rectangular, cubic or other shapes. The magnetic material can be made of samarium cobalt, neodymium iron boron, or a combination thereof, or of like magnetic materials. The magnetic material 13 preferably has a nickel surface treatment to prevent corrosion. The injection port body 11 is preferably made of a silicone elastomer by an injection molding process.

Referring to FIGS. 3 and 4, the elements there shown comprising the injection port assembly 10 may be united using an RTV silicone adhesive or the like. After the adhesive is cured, the injection port body 11 may be adhered, as shown in FIGS. 1 and 2, to a tissue expander shell 31, for example, using a heat compression process.

Figure 5:
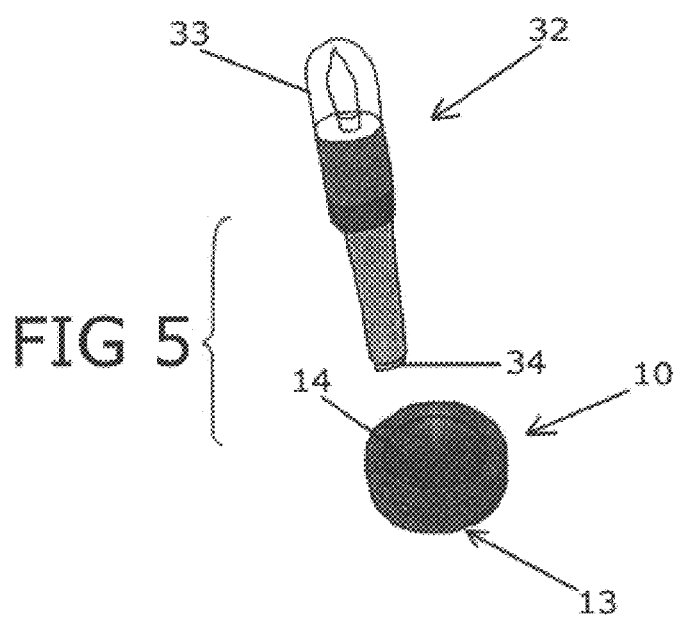
FIG. 5 is a perspective view of a magnetic probe for use with an injection port.

As shown in FIG. 5, the magnetic material 13 and thus the top portion 14 of assembly 10 can be located by a noninvasive or external detection means 32 that is constructed and arranged to sense magnetic fields. The magnetic material 13 has an outer perimeter that is approximately the same as the perimeter of the centrally disposed thickened portion 17 of the injection port top 14. These perimeters are spatially aligned, thus properly demarcating the centrally disposed thickened portion 17 of the injection port top 14 as the target for injecting a hypodermic needle or similar device. External port detection means or magnetic probe 32 is constructed and arranged having a light 33 which illuminates when end 34 senses a magnet or magnetic material underneath the skin.

Figure 6:
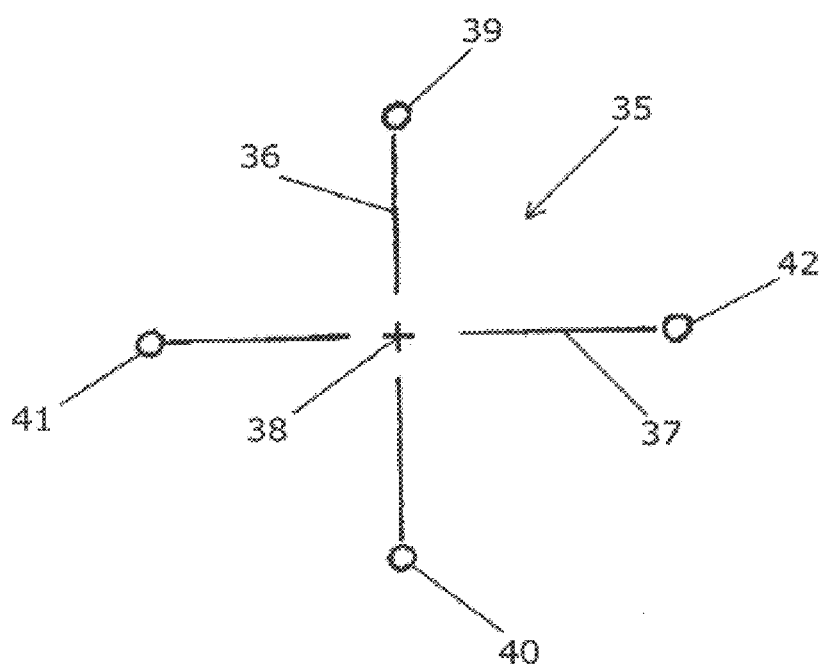
FIG. 6 is a top view of the coordinate system used to locate the magnetic port of the invention.

The precise location of magnetic material 13 and thus the top 14 of the injection port can be determined using a four-direction coordinate system as shown in FIG. 6. FIG. 6 shows a coordinate system 35 that can be used with an external magnetic probe, for example, to locate the top 14 of an injection port. Points 39 and 40 align to form a vertical coordinate 36, while points 41 and 42 align to form a horizontal coordinate 37. The intersection of horizontal coordinate 37 and vertical coordinate 36 forms the center 38 of the coordinate system 35 and is the precise location of the magnetic material 13 and thus the top 14 of the injection port.

As many changes are possible to the embodiments of this invention, utilizing the teachings thereof, the description above and the accompanying drawings should be interpreted in the illustrative and not the limited sense.

That which is claimed:

1. A magnetic injection port assembly comprising:
   a) a formed body having a cavity therein, said body having a top wall, a bottom portion, a peripheral wall, and fluid egress means;
   b) said top wall of said body having a self sealing area comprising a thickened wall area in said top wall of said formed body and further having a rigid ring structure positioned peripherally around said thickened wall area;
   c) a generally dish shaped puncture resistant member disposed at said bottom of said formed body, said puncture resistant member being spacially aligned with said self sealing area; and d) a magnetic field source positioned at said bottom of said body and being spacially positioned entirely below said puncture resistant member and further being spacially aligned with said self sealing area of said top wall.

2. The magnetic injection port assembly of claim 1, wherein said fluid egress means is in communication with a tissue expander.

3. The magnetic injection port assembly of claim 1, wherein said port assembly is sealingly molded into a tissue expander.

4. The magnetic injection port assembly of claim 1, wherein said magnetic source is encapsulated in a polymer.

5. The magnetic injection port assembly of claim 4, wherein said polymer is silicone.

6. The magnetic injection port assembly of claim 1, wherein the magnetic source is comprised of a material selected from the group of materials consisting of somerium cobalt and neodymium iron boron.

7. The magnetic injection port assembly of claim 6, wherein said magnetic source is coated with an anticorrosion material.

8. The magnetic injection port assembly of claim 7, wherein said anticorrosion material coating of said magnetic source is comprised of a nickel layer.

9. The magnetic injection port assembly of claim 1, wherein said magnetic source is comprised of a magnet having a geometric shape.

10. An injection port assembly for use with a tissue expander system and similar inflatable medical devices, said assembly comprising:
    a) a body having a top portion being self-sealing to punctures by a hypodermic needle, an outside lateral wall and a bottom portion, wherein said top portion has a centrally disposed thickened portion having a perimeter;
    b) a needle guard assembly and a ring member surrounding said centrally disposed thickened portion of said self-sealing top portion, whereby said top portion, said ring member and said needle guard assembly forming an injection port cavity;
    c) a magnetic material positioned in said assembly, and being disposed below said needle guard assembly and outside said injection port cavity; and
    d) a means of fluid communication from said injection port to the medical device.

11. The assembly of claim 10, whereby said magnetic material is disc-shaped and whereby said magnetic material has an outer perimeter that is spatially aligned with said perimeter of said centrally disposed thickened portion of said top portion.

12. The assembly of claim 10, wherein said magnetic material is selected from a group of magnetic materials consisting of samarium cobalt, neodymium iron boron, and a combination thereof.

13. The assembly of claim 10, wherein said magnetic material is encapsulated in a polymer.

14. The assembly of claim 13, wherein said polymer is a biocompatible silicone elastomer.

15. The assembly of claim 10, wherein said magnetic material is encapsulated in said bottom portion of said assembly.

16. The assembly of claim 10, wherein said magnetic material further has an anti-corrosive surface treatment comprised of nickel.

17. The assembly of claim 10, wherein said injection port body is made of a biocompatible silicone elastomer and is formed by an injection molding process.

18. The assembly of claim 10, wherein the cross-sectional shape of said bottom is generally hemispherical.

19. A tissue expander system having a magnetic injection port assembly comprising:
    a) a tissue expander shell;
    b) an injection port assembly sealingly attached to said tissue expander shell, said injection port assembly further comprising:
        i) a body having a self-sealing top portion, a lateral wall, and a bottom portion forming an injection port cavity, said self-sealing top portion including a centrally disposed thickened area;
        ii) a dish shaped needle guard structure having a specified area disposed at said bottom portion of said body;
        iii) a rigid ring member disposed adjacent said lateral wall and surrounding said thickened area of said self sealing top portion; and
        iv) a magnetic material having an area smaller than said specified area of said needle guard structure, said magnetic material being positioned in said bottom portion and below said needle guard structure and outside said injection port cavity, said dish shaped needle guard structure spanning generally the entire bottom portion and covering said magnetic material; and
    c) fluid communication means in said body connecting said tissue expander shell and said injection port cavity.

20. The injection port assembly of claim 19, wherein said rigid ring member is constructed of stainless steel and wherein said dish shaped needle guard structure is constructed of a puncture resistant material selected from the group of materials consisting of stainless steel and para-aramid fiber material.

* * * * *